(12) United States Patent
Fu

(10) Patent No.: US 11,313,569 B2
(45) Date of Patent: Apr. 26, 2022

(54) INTELLIGENT AIR PURIFICATION ROBOT WITH MOSQUITO-REPELLING FUNCTION

(71) Applicant: Dongguan Weibo Electronic Technology Co., Ltd., Dongguan (CN)

(72) Inventor: Xiaofeng Fu, Hubei (CN)

(73) Assignee: DONGGUAN WEIBO ELECTRONIC TECHNOLOGY CO., LTD., Dongguan (CN)

( * ) Notice: Subject to any disclaimer, the term of this patent is extended or adjusted under 35 U.S.C. 154(b) by 169 days.

(21) Appl. No.: 16/861,240

(22) Filed: Apr. 29, 2020

(65) Prior Publication Data

US 2020/0288694 A1    Sep. 17, 2020

(51) Int. Cl.
| | |
|---|---|
| *A01M 29/12* | (2011.01) |
| *F24F 8/22* | (2021.01) |
| *G05D 1/02* | (2020.01) |
| *A61L 9/20* | (2006.01) |
| *A61L 9/015* | (2006.01) |
| *F24F 8/108* | (2021.01) |

(52) U.S. Cl.
CPC ............... *F24F 8/22* (2021.01); *A01M 29/12* (2013.01); *A61L 9/015* (2013.01); *A61L 9/205* (2013.01); *G05D 1/0214* (2013.01); *A61L 2209/11* (2013.01); *A61L 2209/135* (2013.01); *A61L 2209/14* (2013.01); *A61L 2209/212* (2013.01); *A61L 2209/22* (2013.01); *F24F 8/108* (2021.01); *F24F 2221/42* (2013.01)

(58) Field of Classification Search
CPC .... A01M 29/12; A01M 29/00; G05D 1/0214; F24F 8/108; F24F 8/22; F24F 8/26; F24F 2221/42; A61L 9/015; A61L 9/205; A61L 2209/11; A61L 2209/135; A61L 2209/14; A61L 2209/212; A61L 2209/22
USPC .......................................................... 43/129
See application file for complete search history.

(56) References Cited

FOREIGN PATENT DOCUMENTS

| | | | | | |
|---|---|---|---|---|---|
| CN | 109185993 | A | * | 1/2019 | ............ F24F 8/108 |
| CN | 208817924 | U | * | 5/2019 | ............ F26B 11/18 |
| CN | 110425650 | A | * | 11/2019 | ............ F24F 8/108 |
| CN | 110701701 | A | * | 1/2020 | ............ F24F 8/108 |
| DE | 4410476 | A1 | * | 10/1994 | ............ A61L 9/03 |
| KR | 20170095142 | A | * | 8/2017 | ............ A01M 1/06 |
| WO | WO-2019080943 | A1 | * | 5/2019 | ......... A01D 34/008 |

\* cited by examiner

*Primary Examiner* — Peter M Poon
*Assistant Examiner* — Mohamed Aboukoura

(57) ABSTRACT

The present application provides an intelligent air purification robot with a mosquito-repelling function. In the present application, a robot body has an obstacle detection function and can make a turn automatically. That is, the robot body can automatically find a path after being placed in a room, and can purify air everywhere in the room. Dust-laden air enters a housing from an air inlet and is then treated by a plurality of modular units. Moreover, a UV lamp is further provided, so that air can be disinfected at a designated position.

10 Claims, 5 Drawing Sheets

INTELLIGENT AIR PURIFICATION ROBOT WITH MOSQUITO-REPELLING FUNCTION

BACKGROUND OF THE INVENTION

The present utility model relates to the field of air purifiers, and in particular to an intelligent air purification robot with a mosquito-repelling function.

With the development of urbanization, more and more vehicles use fuel as raw materials, and industries are more and more developed. As a result, the air pollution is increasingly serious with the content of harmful gases such as carbon monoxide and sulfur dioxide in air getting higher and higher, and phenomena such as global warming and greenhouse effect are more obvious. Particularly, air in first-tier cities and second-tier cities is getting worse. As people's pursuit for living quality is constantly improved, more and more attention is paid to air purification. Particularly, sedentary people in the office pay more attention to a comfortable air environment. However, air fresheners are mostly used at the present, but no obvious effect is achieved. Moreover, chemical materials are used in the air fresheners, so the original smell of air is covered by perfume, resulting in certain hazards to persons with asthma, allergic condition and allergic diseases in case of frequent use.

There are various air purifiers available in the market, but the air purifiers in the prior art still have the following technical problems. Firstly, the air purifiers in the prior art are stationary and can only be fixed at a certain position, so the purification efficiency is low. Secondly, the air purifiers in the prior art have a single function, i.e., the most basic air purification function, so consumers' requirements cannot be satisfied. Thirdly, due to the integration of modules, it is difficult to maintain and replace, and it is also difficult to clean.

BRIEF SUMMARY OF THE INVENTION

To solve the above problems, the present utility model provides an intelligent air purification robot with a mosquito-repelling function, which realizes air purification in a moving manner, is convenient to maintain and replace since the modular units therein are assembled detachably, and has a mosquito-repelling function.

For this purpose, the present utility model employs the following technical solutions. An intelligent air purification robot with a mosquito-repelling function is provided, including a robot body that has an obstacle detection function and can make a turn automatically, characterized in that the robot body includes a housing with an air inlet and an air outlet, an insecticidal purification component arranged in the housing, a power supply unit arranged in the housing, and a main control board that is electrically connected to the power supply unit and arranged in the housing; the insecticidal purification component includes a front filter screen, a fan unit, a black light lamp unit, a photocatalytic layer unit, an anion generator, an ozone generator and an electric mosquito-repelling liquid evaporation unit; the front filter screen is detachably mounted at the air inlet, and both the anion generator and the ozone generator are detachably mounted at the air outlet; several pairs of mounting seats that are symmetrical in an up-down direction are arranged in the robot body, and mounting holes corresponding to the mounting seats are formed in a sidewall of the robot body; the photocatalytic layer unit, the black light lamp unit, the electric mosquito-repelling liquid evaporation unit and the fan unit are successively arranged in parallel in a direction from the air inlet to the air outlet, and pass through the mounting holes to be detachably mounted on the respective mounting seats; the black light lamp unit, the fan unit and the electric mosquito-repelling liquid evaporation unit are all electrically connected to the main control board; the insecticidal purification component further includes a hollow electric telescopic rod component; one end of the electric telescopic rod component is electrically connected to the main control board, and the other end thereof extends outside the housing to be connected to a UV lamp; and, the UV lamp passes through the inside of the electric telescopic rod component through a lead wire and is electrically connected to the main control board.

Further, a groove, which extends along the length of the mounting seat and has a longitudinal section shaped as an isosceles trapezoid, is formed on the surface of each mounting seat; the fan unit includes an exhaust fan and horizontal fan mounting frames mounted at upper and lower ends of the exhaust fan; each fan horizontal mounting frame has a longitudinal section matched with that of the groove; and, the horizontal fan mounting frames at the upper and lower ends of the exhaust fan are inserted into the grooves on the mounting seats and slide along the grooves.

Further, a first fan vertical mounting frame is mounted on one side of the exhaust fan, a fan quick-fit male terminal is arranged on the first fan vertical mounting frame, and the exhaust fan is electrically connected to the fan quick-fit male terminal; a fan quick-fit female terminal corresponding to the fan quick-fit male terminal is arranged on the main control board; a second fan vertical mounting frame is mounted on the other side of the exhaust fan; the fan horizontal mounting frames at the upper and lower ends of the exhaust fan pass through the mounting holes to be inserted into the grooves on the mounting seats; the fan quick-fit male terminal is electrically connected to the fan quick-fit female terminal; and, the second fan vertical mounting frame is hermetically arranged in the mounting holes.

Further, a fan push-pull handle is further arranged on a side of the second fan vertical mounting frame facing the outside of the housing.

Further, the black light lamp unit includes a sealing cover plate, a mounting cover plate, and a plurality of black light lamps that extend along a lengthwise direction of the mounting seats and arranged from the top down; clamping slots equal in number to the black light lamps are formed on one side of the mounting cover plate, and the sealing cover plate is fixed on the other side of the mounting cover plate; one end of each of the plurality of black light lamps is inserted into the clamping slot, and a black light lamp quick-fit male terminal is arranged at the other end of the black light lamp; black light lamp quick-fit female terminals corresponding to the black light lamp quick-fit male terminals are arranged on the main control board; upper and lower ends of the mounting cover plate have longitudinal sections of an isosceles trapezoid structure; the upper and lower ends of the mounting cover plate are inserted into the grooves on the mounting seats; the black light lamp quick-fit male terminals of the black light lamps are electrically connected to the black light lamp quick-fit female terminals; and, the sealing cover plate is hermetically covered on the mounting holes.

Further, a black light lamp push-pull handle is further arranged on a side of the sealing cover plate facing the outside of the housing.

Further, the electric mosquito-repelling liquid evaporation unit includes a support grid, an electric mosquito-repelling liquid evaporator, and mosquito-repelling horizontal mounting frames mounted at upper and lower ends of the support grid, and the mosquito-repelling horizontal mounting frames have longitudinal sections matched with that of the grooves; a first mosquito-repelling vertical mounting frame is mounted on one side of the support grid; a mosquito-repelling quick-fit male terminal is arranged on the first mosquito-repelling vertical mounting frame; a clamping hole for clamping the electric mosquito-repelling liquid evaporator is formed in the center of the support grid; the electric mosquito-repelling liquid evaporator is clamped in the clamping hole and electrically connected to the mosquito-repelling quick-fit male terminal through a lead wire; a mosquito-repelling quick-fit female terminal corresponding to the mosquito-repelling quick-fit male terminal is arranged on the main control board; a second mosquito-repelling vertical mounting frame is mounted on the other side of the support grid; the mosquito-repelling horizontal mounting frame is inserted into the grooves on the mounting seats and slide along the grooves; the mosquito-repelling quick-fit male terminal is electrically connected to the mosquito-repelling quick-fit female terminal; the second mosquito-repelling vertical mounting frame is hermetically arranged in the mounting holes; and, a mosquito-repelling push-pull handle is arranged on a side of the second mosquito-repelling vertical mounting frame facing the outside of the housing.

Further, the photocatalytic layer unit includes an activated carbon fiber mesh coated with a TiO2 photocatalyst; photocatalytic layer horizontal mounting frames are mounted at upper and lower ends of the activated carbon fiber mesh, and the photocatalytic layer horizontal mounting frames have longitudinal sections matched with that of the grooves; a first photocatalytic layer vertical mounting frame is mounted on one side of the activated carbon fiber mesh, and a second photocatalytic layer vertical mounting frame is mounted on the other side of the electric mosquito-repelling liquid evaporator; the photocatalytic layer horizontal mounting frames located at the upper and lower ends of the activated carbon fiber mesh are inserted into the grooves on the mounting seats and slide along the grooves; the second photocatalytic layer vertical mounting frame is hermetically arranged in the mounting holes; and, a photocatalytic layer push-pull handle is arranged on a side of the second photocatalytic layer vertical mounting frame facing the outside of the housing.

Further, a WIFI unit is further arranged in the housing, and the WIFI unit is in bidirectional communication with the main control board.

Further, a cylindrical sleeve is helically mounted at the air inlet in the housing; internal threads are formed on an inner wall of the cylindrical sleeve; an external thread is formed on an outer sidewall of the front filter screen; and, the external thread on the front filter screen is fitted with the internal threads on the inner wall of the cylindrical sleeve to realize detachable connection.

The present utility model has the following beneficial effects.

1. In the present application, the robot body has an obstacle detection function and can make a turn automatically. That is, the robot body can automatically find a path after being placed in a room, and can purify air everywhere in the room.

2. A front filter screen, a fan unit, a black light lamp unit, a photocatalytic layer unit, an anion generator, an ozone generator and an electric mosquito-repelling liquid evaporation unit are arranged in the robot body. By activating the fan unit, dust-laden air enters the housing from the air inlet, and successively passes through the front filter screen, the photocatalytic layer unit, the black light lamp unit, the electric mosquito-repelling liquid evaporation unit, the anion generator and the ozone generator. Dust in the air is preliminarily removed by the front filter screen. By the cooperation of the black light lamp unit with the photocatalytic layer and the adsorption performance of the photocatalytic layer unit, low-concentration organic pollutants in air in the room are quickly adsorbed. Thus, volatile organic pollutants are gathered on the carrier activated carbon fiber mesh, and then photocatalyzed in situ on the surface of the TiO2 catalyst loaded on the activated carbon fiber mesh. The low-concentration volatile organic pollutants are effectively photocatalyzed until they are completely converted into harmless carbon dioxide, water and simple inorganic matters, and the activated carbon fiber mesh is continuously regenerated in situ. This process is efficient and free of secondary pollution. The electric mosquito-repelling liquid evaporation unit is arranged in front of the fan unit. By evaporating and discharging the electric mosquito-repelling liquid out from the housing, the mosquito repelling effect can be effectively achieved. Anions are generated by the anion generator, and a trace amount of ozone is generated by the ozone generator. Based on a two-in-one purification principle, the effects of decomposing formaldehyde, benzene, methylbenzene and dimethylbenzene, killing bacteria, eliminating odor and cleaning air can be effectively achieved. Only the treated air will be discharged into the room. Moreover, an electric telescopic rod is further provided, which is connected to a UV lamp. Thus, the electric telescopic rod can be controlled to extend or retract by the main control board, so that the UV lamp can reach a designated position for disinfection.

3. The photocatalytic layer unit, the black light lamp unit, the electric mosquito-repelling liquid evaporation unit and the fan unit are successively arranged in parallel in a direction from the air inlet to the air outlet, and pass through the mounting holes to be detachably mounted on respective mounting bases. Moreover, the front filter screen is detachably mounted at the air inlet, and both the anion generator and the ozone generator are detachably mounted at the air outlet. That is, the modular units in the housing can be conveniently disassembled and taken out, so it is convenient to clean, maintain and replace.

Figure 1:
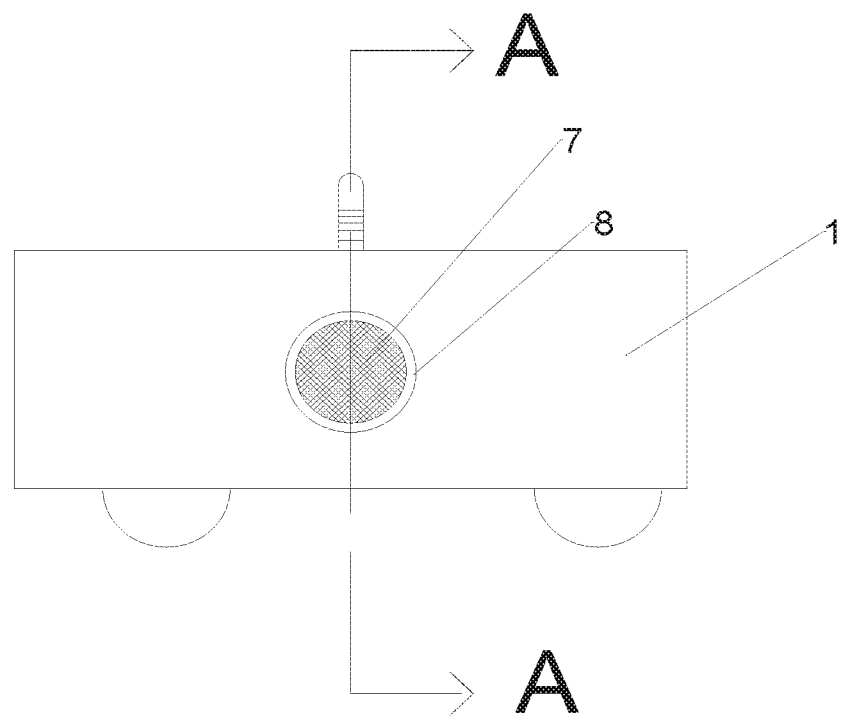
FIG. 1 is a right schematic structural view of the present utility model.
Figure 2:
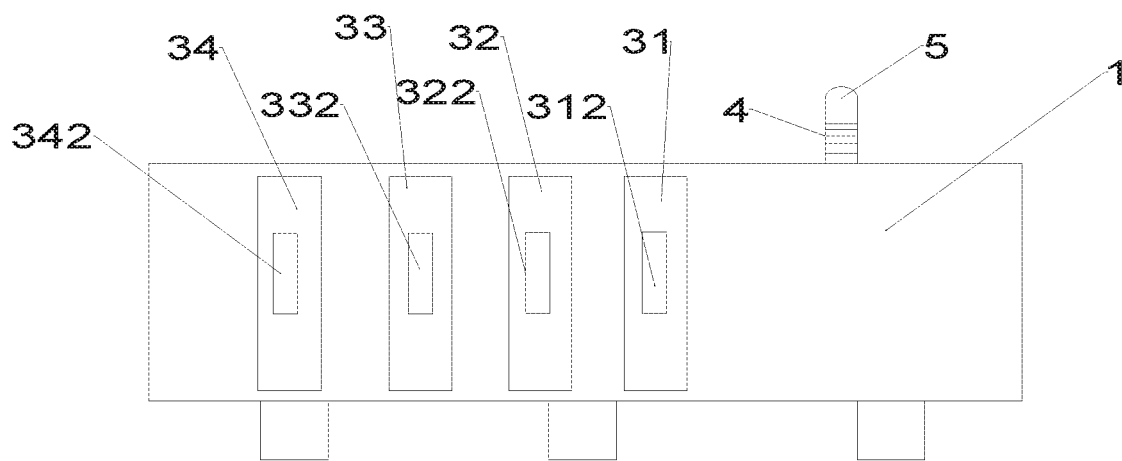
FIG. 2 is a front schematic structural view of the present utility model.
Figure 3:
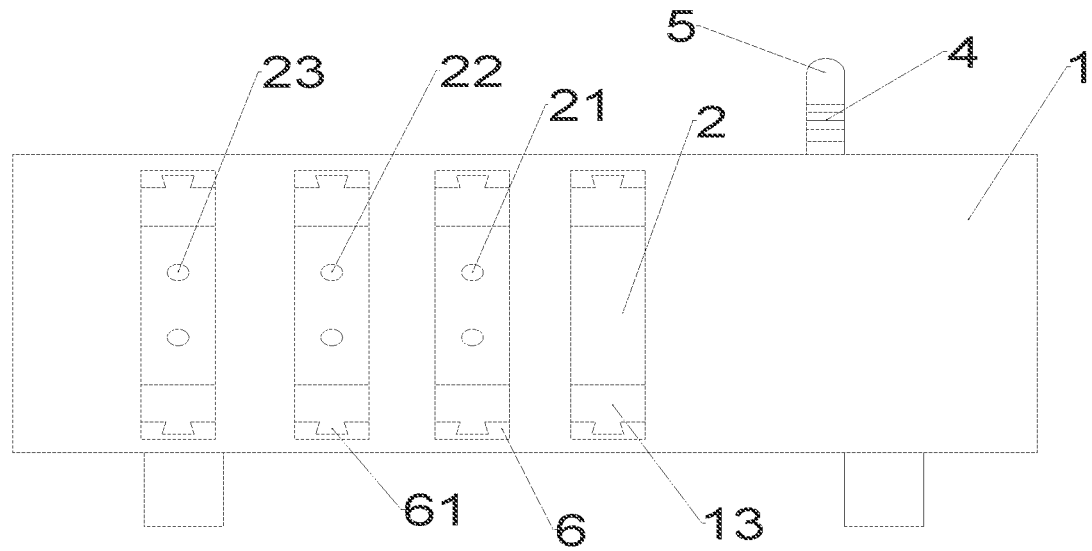
FIG. 3 is a front schematic structural view of the present utility model with the modular units omitted.
Figure 4:
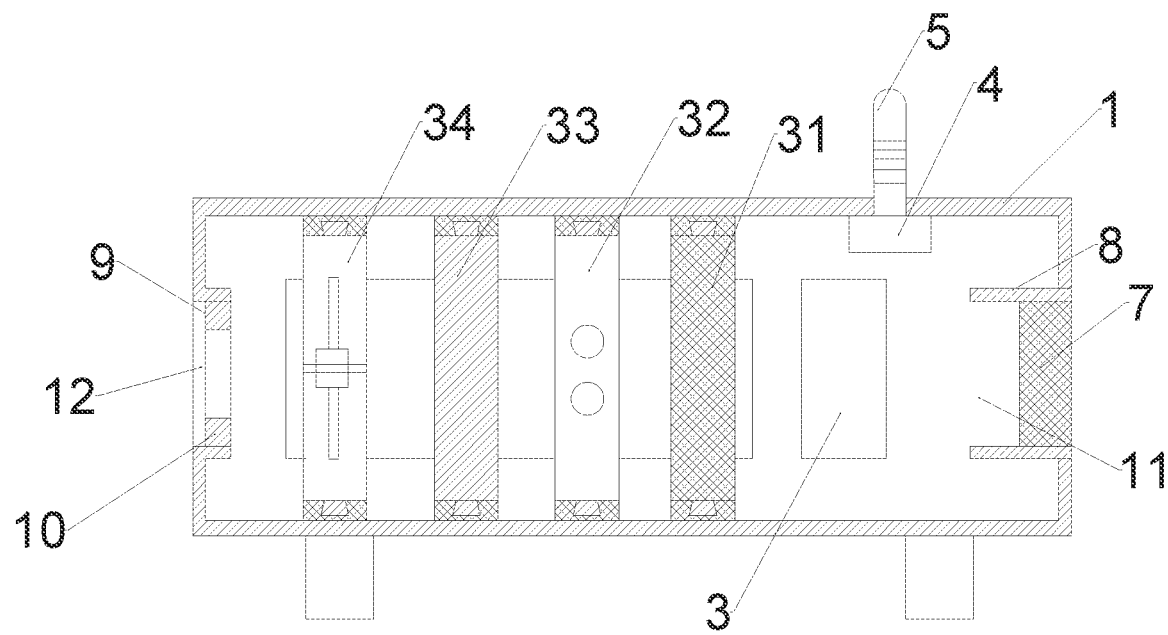
FIG. 4 is a sectional view of FIG. 1 along a section line A-A.
Figure 5:
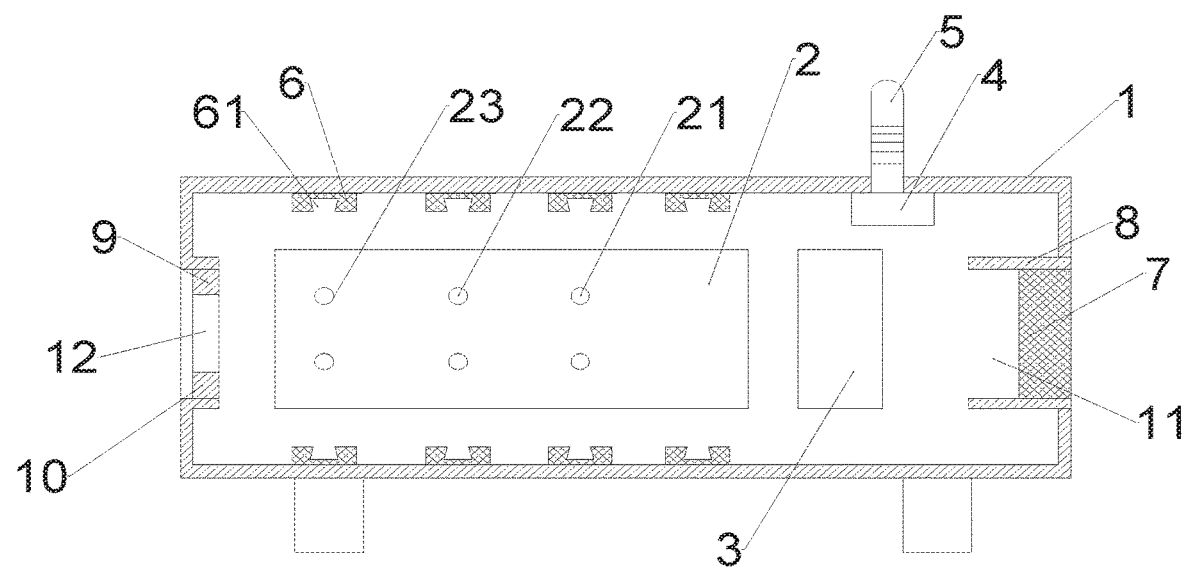
FIG. 5 is a structural view of FIG. 4 with the modular units omitted.
Figure 6:
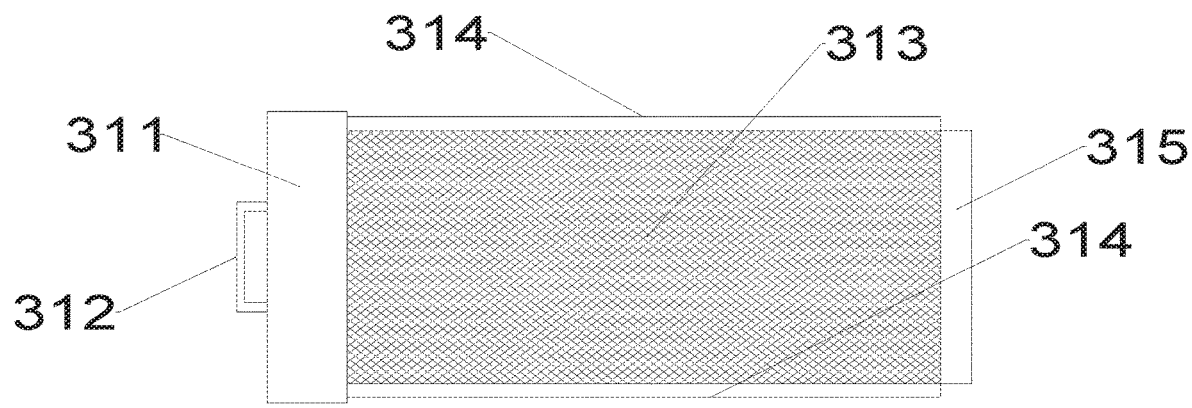
FIG. 6 is a structural view of a photocatalytic layer unit according to the present utility model.
Figure 7:
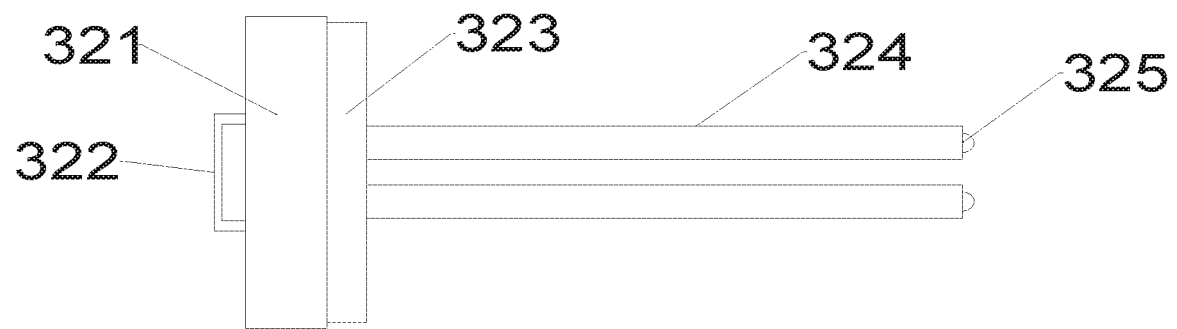
FIG. 7 is a structural view of a black light lamp unit according to the present utility model.
Figure 8:
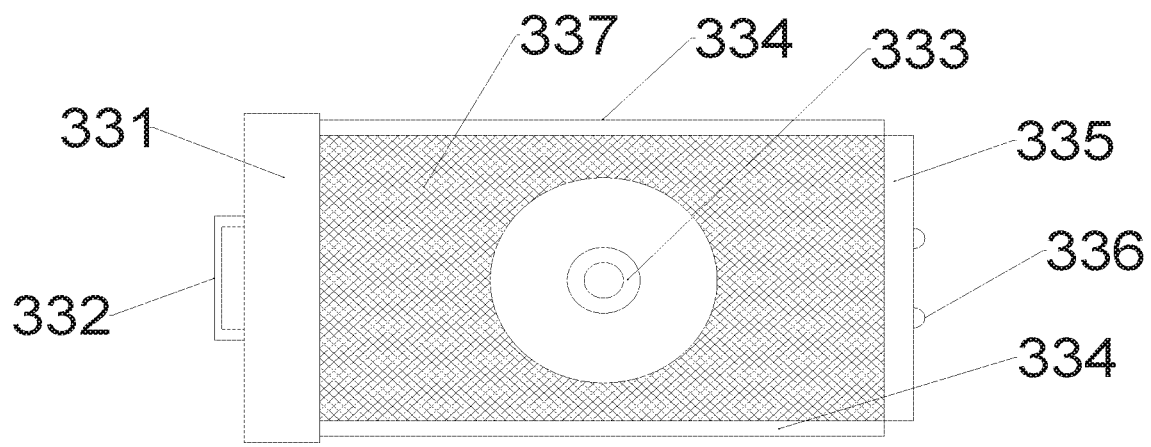
FIG. 8 is a structural view of an electric mosquito-repelling liquid evaporation unit according to the present utility model.
Figure 9:
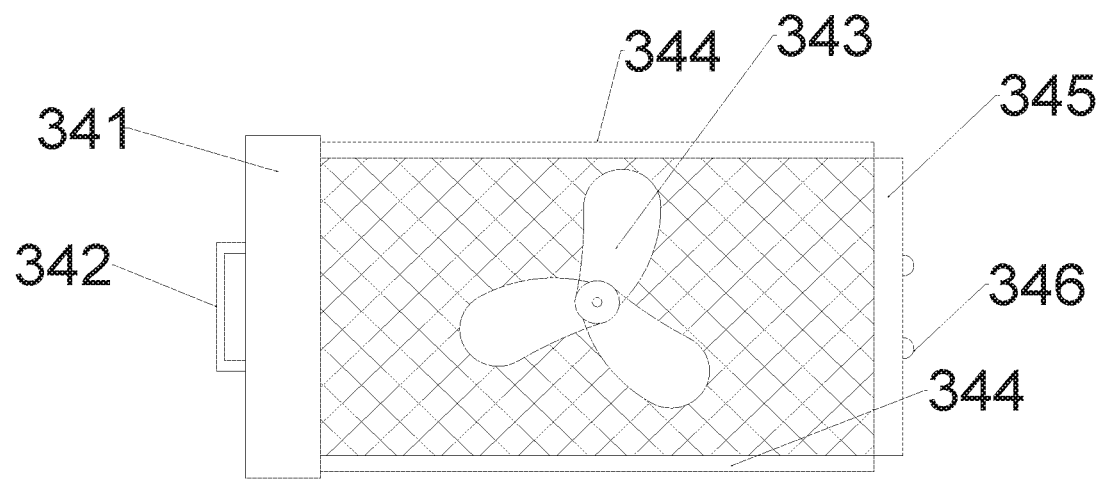
FIG. 9 is a structural view of a fan unit according to the present utility model.

in which:

1: robot body; 2: main control board; 21: black light lamp quick-fit female terminal; 22: mosquito-repelling quick-fit female terminal; 23: fan quick-fit female terminal; 3: power supply unit; 31: photocatalytic layer unit; 311: second photocatalytic layer vertical mounting frame; 312: photocatalytic layer push-pull handle; 313: activated carbon fiber mesh; 314: photocatalytic layer horizontal mounting frame; 315: first photocatalytic layer vertical mounting frame; 32: black light lamp unit; 321: sealing cover plate; 322: black light lamp push-pull handle; 323: mounting cover plate; 324: black light lamp; 325: black light lamp quick-fit male terminal; 33: electric mosquito-repelling liquid evaporation unit; 331: second mosquito-repelling vertical mounting frame; 332: mosquito-repelling push-pull handle; 333: electric mosquito-repelling liquid evaporator; 334: mosquito-repelling horizontal mounting frame; 335: first mosquito-repelling vertical mounting frame; 336: mosquito-repelling quick-fit male terminal; 337: support grid; 34: fan unit; 341: second fan vertical mounting frame; 342: fan push-pull handle; 343: exhaust fan; 344: fan horizontal mounting frame 344; 345: first fan vertical mounting frame; 346: fan quick-fit male terminal; 4: electric telescopic rod component; 5: UV lamp; 6: mounting seat; 61: groove; 7: front filter screen; 8: cylindrical sleeve; 9: anion generator; 10: ozone generator; 11: air inlet; 12: air outlet; and, 13: mounting hole.

DETAILED DESCRIPTION OF THE INVENTION

With reference to FIGS. 1-10, the present utility model provides an intelligent air purification robot with a mosquito-repelling function, including a robot body 1 that has an obstacle detection function and can make a turn automatically. The robot body 1 includes a housing with an air inlet 11 and an air outlet 12, an insecticidal purification component arranged in the housing, a power supply unit 3 arranged in the housing, and a main control board 2 that is electrically connected to the power supply unit 3 and arranged in the housing. The insecticidal purification component includes a front filter screen 7, a fan unit 34, a black light lamp unit 32, a photocatalytic layer unit 31, an anion generator 9, an ozone generator 10 and an electric mosquito-repelling liquid evaporation unit 33. The front filter screen 7 is detachably mounted at the air inlet 11, and both the anion generator 9 and the ozone generator 10 are detachably mounted at the air outlet 12. Several pairs of mounting seats 6 that are symmetrical in an up-down direction are arranged in the robot body 1, and mounting holes 13 corresponding to the mounting seats 6 are formed in a sidewall of the robot body 1. The photocatalytic layer unit 31, the black light lamp unit 32, the electric mosquito-repelling liquid evaporation unit 33 and the fan unit 34 are successively arranged in parallel in a direction from the air inlet 11 to the air outlet 12, and pass through the mounting holes 13 to be detachably mounted on respective mounting seats 6. The black light lamp unit 32, the fan unit 34 and the electric mosquito-repelling liquid evaporation unit 33 are all electrically connected to the main control board 2. The insecticidal purification component further includes a hollow electric telescopic rod component 4. One end of the electric telescopic rod component 4 is electrically connected to the main control board 2, and the other end thereof extends outside the housing to be connected to a UV lamp 5. The UV lamp 5 passes through the inside of the electric telescopic rod component 4 through a lead wire and is electrically connected to the main control board 2.

In the present application, the robot body 1 has an obstacle detection function and can make a turn automatically. That is, the robot body can automatically find a path after being placed in a room, and can purify air everywhere in the room.

The front filter screen 7, the fan unit 34, the black light lamp unit 32, the photocatalytic layer unit 31, the anion generator 9, the ozone generator 10 and the electric mosquito-repelling liquid evaporation unit 33 are arranged in the robot body 1. By activating the fan unit 34, dust-laden air enters the housing from the air inlet 11, and successively passes through the front filter screen 7, the photocatalytic layer unit 31, the black light lamp unit 32, the electric mosquito-repelling liquid evaporation unit 33, the fan unit 34, the anion generator 9 and the ozone generator 10. Dust in the air is preliminarily removed by the front filter screen 7. By the cooperation of the black light lamp unit 32 with the photocatalytic layer 31 and the adsorption performance of the photocatalytic layer unit 31, low-concentration organic pollutants in air in the room are quickly adsorbed. Thus, volatile organic pollutants are gathered on the carrier activated carbon fiber mesh 313, and then photocatalyzed in situ on the surface of the $TiO_2$ catalyst loaded on the activated carbon fiber mesh 313. The low-concentration volatile organic pollutants are effectively photocatalyzed until they are completely converted into harmless carbon dioxide, water and simple inorganic matters, and the activated carbon fiber mesh 313 is continuously regenerated in situ. This process is efficient and free of secondary pollution. The electric mosquito-repelling liquid evaporation unit 33 is arranged in front of the fan unit 34. By evaporating and discharging the electric mosquito-repelling liquid out from the housing, the mosquito repelling effect can be effectively achieved. Anions are generated by the anion generator 9, and a trace amount of ozone is generated by the ozone generator 10. Based on a two-in-one purification principle, the effects of decomposing formaldehyde, benzene, methylbenzene and dimethylbenzene, killing bacteria, eliminating odor and cleaning air can be effectively achieved. Moreover, an electric telescopic rod is further provided, which is connected to a UV lamp 5. Thus, the electric telescopic rod can be controlled to extend or retract by the main control board, so that the UV lamp 5 can reach a designated position for disinfection. It is to be noted that the electric telescopic rod component is a conventional telescopic rod structure, and therefore the specific structure thereof will not be repeated here.

The photocatalytic layer unit 31, the black light lamp unit 32, the electric mosquito-repelling liquid evaporation unit 33 and the fan unit 34 are successively arranged in parallel in a direction from the air inlet 11 to the air outlet 12, and pass through the mounting holes 13 to be detachably mounted on respective mounting bases 6. Moreover, the front filter screen 7 is detachably mounted at the air inlet 11, and both the anion generator 9 and the ozone generator 10 are detachably mounted at the air outlet 12. That is, the modular units in the housing can be conveniently disassembled and taken out, so it is convenient to clean, maintain and replace, and the growth of bacteria is effectively reduced.

Further, a groove 61, which extends along the length of the mounting seat 6 and has a longitudinal section shaped as an isosceles trapezoid, is formed on the surface of each mounting seat 6. The fan unit 34 includes an exhaust fan 343 and horizontal fan mounting frames 344 mounted at upper and lower ends of the exhaust fan 343. Each fan horizontal mounting frame 344 has a longitudinal section matched with that of the groove 61. The horizontal fan mounting frames 344 at the upper and lower ends of the exhaust fan 343 are inserted into the grooves 61 on the mounting seats 6 and slide along the grooves 61. Further, a first fan vertical mounting frame 345 is mounted on one side of the exhaust fan 343, a fan quick-fit male terminal 346 is arranged on the first fan vertical mounting frame 345, and the exhaust fan 343 is electrically connected to the fan quick-fit male terminal 346. A fan quick-fit female terminal 23 corresponding to the fan quick-fit male terminal 346 is arranged on the main control board 2. A second fan vertical mounting frame 341 is mounted on the other side of the exhaust fan 343. The fan horizontal mounting frames 344 at the upper and lower ends of the exhaust fan 343 pass through the mounting holes 13 to be inserted into the grooves 61 on the mounting seats 6. The fan quick-fit male terminal 346 is electrically connected to the fan quick-fit female terminal 23. The second fan vertical mounting frame 341 is hermetically arranged in the mounting holes 13.

Since the mounting frames have longitudinal sections of an isosceles trapezoid structure, deflection of each unit in the housing in a vertical direction can be avoided, that is, the mounting frames are prevented from falling off the grooves 61 on the mounting seats 6. Moreover, in the preset application, in the fan unit 34, the fan quick-fit male terminal 346 can be electrically connected to the fan quick-fit female terminal 23 by directly inserting the fan mesh mounting holes 13 into the grooves 61 on the mounting seats 6, so that the positioning of the fan and the circulation connection can be realized. Moreover, since the second fan vertical mounting frame 341 is hermetically arranged in the mounting holes 13, the internal sealing performance of the housing can be ensured.

Further, a fan push-pull handle 342 is further arranged on a side of the second fan vertical mounting frame 341 facing the outside of the housing. When it is required to replace, maintain or clean the fan, it is only necessary to pull the fan unit 34 out from the housing by pulling the fan push-pull handle 342.

Further, the black light lamp unit 32 includes a sealing cover plate 321, a mounting cover plate 323, and a plurality of black light lamps 324 that extend along a lengthwise direction of the mounting seats 6 and arranged from the top down. Clamping slots equal in number to the black light lamps 324 are formed on one side of the mounting cover plate 323, and the sealing cover plate 321 is fixed on the other side of the mounting cover plate 323. One end of each of the plurality of black light lamps 324 is inserted into the clamping slot, and a black light lamp quick-fit male terminal 325 is arranged at the other end of the black light lamp 324. Black light lamp quick-fit female terminals 21 corresponding to the black light lamp quick-fit male terminals 325 are arranged on the main control board 2. Upper and lower ends of the mounting cover plate 323 have longitudinal sections of an isosceles trapezoid structure. The upper and lower ends of the mounting cover plate 323 are inserted into the grooves 61 on the mounting seats 6. The black light lamp quick-fit male terminals 325 of the black light lamps 324 are electrically connected to the black light lamp quick-fit female terminals 21. The sealing cover plate 321 is hermetically covered on the mounting holes 13. The principle of assembling the black light lamp unit 32 with the housing is similar to that of the fan unit 34. The black light lamps 324 are fixed to the mounting cover plate 323 by being inserted into the clamping slots. After the black light lamp unit 32 is mounted on respective mounting seats 6, the black light lamp quick-fit male terminals 325 of the black light lamps 324 are electrically connected to the black light lamp quick-fit female terminals 21, so that quick withdraw/insertion and circuit connection can be realized, making the maintenance, replacement and cleaning more convenient.

Further, a black light lamp push-pull handle 322 is further arranged on a side of the sealing cover plate 321 facing the outside of the housing. Similarly, when it is required to replace, maintain or clean the black light lamps 324, it is only necessary to pull the black light lamp 32 out from the housing by pulling the black light lamp push-pull handle 322.

Further, the electric mosquito-repelling liquid evaporation unit 33 includes a support grid 337, an electric mosquito-repelling liquid evaporator 333, and mosquito-repelling horizontal mounting frames 334 mounted at upper and lower ends of the support grid 337, wherein the mosquito-repelling horizontal mounting frames 334 have longitudinal sections matched with that of the grooves 61. A first mosquito-repelling vertical mounting frame 335 is mounted on one side of the support grid 337. A mosquito-repelling quick-fit male terminal 336 is arranged on the first mosquito-repelling vertical mounting frame 335. A clamping hole for clamping the electric mosquito-repelling liquid evaporator 333 is formed in the center of the support grid 337. The electric mosquito-repelling liquid evaporator 333 is clamped in the clamping hole and electrically connected to the mosquito-repelling quick-fit male terminal 336 through a lead wire. A mosquito-repelling quick-fit female terminal 22 corresponding to the mosquito-repelling quick-fit male terminal 336 is arranged on the main control board 2. A second mosquito-repelling vertical mounting frame 331 is mounted on the other side of the support grid 337. The mosquito-repelling horizontal mounting frame 334 is inserted into the grooves 61 on the mounting seats 6 and slide along the grooves 61. The mosquito-repelling quick-fit male terminal 336 is electrically connected to the mosquito-repelling quick-fit female terminal 22. The second mosquito-repelling vertical mounting frame 331 is hermetically arranged in the mounting holes 13, and a mosquito-repelling push-pull handle 332 is arranged on a side of the second mosquito-repelling vertical mounting frame 331 facing the outside of the housing.

The structure of the electric mosquito-repelling liquid evaporation unit 33 is similar to that of the fan unit 34. The electric mosquito-repelling liquid evaporation unit 33 can be quickly withdrawn from or inserted into the respective mounting seat 6 by using the mosquito-repelling push-pull handle 332, to achieve the fixation of the electric mosquito-repelling liquid evaporation unit 33 in the housing and the circuit connection. Moreover, in the electric mosquito-repelling liquid evaporation unit 33, the electric mosquito-repelling liquid evaporation unit 33 will not block the flow of gas due to the provision of the support grid 337.

Further, the photocatalytic layer unit 31 includes an activated carbon fiber mesh 313 coated with a TiO2 photocatalyst. Photocatalytic layer horizontal mounting frames 314 are mounted at upper and lower ends of the activated carbon fiber mesh 313, and the photocatalytic layer horizontal mounting frames 314 have longitudinal sections matched with that of the grooves 61. A first photocatalytic layer vertical mounting frame 315 is mounted on one side of the activated carbon fiber mesh 313, and a second photocatalytic layer vertical mounting frame 311 is mounted on the other side of the activated carbon fiber mesh 313. The photocatalytic layer horizontal mounting frames 314 located at the upper and lower ends of the activated carbon fiber mesh 313 are inserted into the grooves 61 on the mounting seats 6 and slide along the grooves 61. The second photocatalytic layer vertical mounting frame 311 is hermetically arranged in the mounting holes 13, and a photocatalytic layer push-pull handle 312 is arranged on a side of the second photocatalytic layer vertical mounting frame 311 facing the outside of the housing.

It is to be noted, during the replacement of the fan unit 34, the black light unit 32, the photocatalytic layer unit 31 and the electric mosquito-repelling liquid evaporation unit 33, corresponding cover plates may be covered on the corresponding mounting holes 13 to prevent dust from entering the housing through the mounting holes 13.

The air purifier uses the activated carbon fiber mesh 313 as a carrier-loaded TiO2 (titanium dioxide) catalyst. Low-concentration organic pollutants in air in the room are quickly adsorbed due to the adsorption performance of the activated carbon fiber mesh. Thus, volatile organic pollutants are gathered on the carrier activated carbon fiber mesh 313, and then irradiated by the black light lamp unit 32, and photocatalyzed in situ on the surface of the TiO2 catalyst loaded on the activated carbon fiber mesh 313. The low-concentration volatile organic pollutants are effectively photocatalyzed until they are completely converted into harmless carbon dioxide, water and simple inorganic matters, and the activated carbon fiber mesh 313 is continuously regenerated in situ. This process is efficient and free of secondary pollution.

Figure 10:
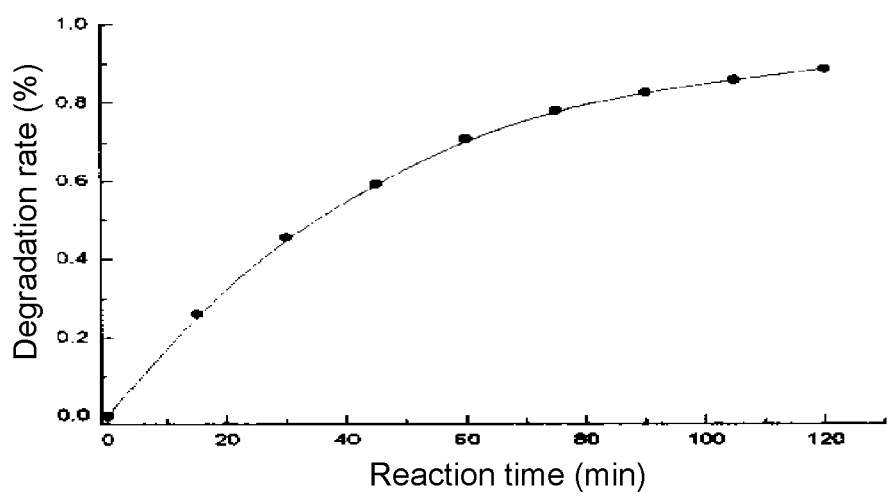
FIG. 10 is a kinetic curve based on photocatalytic degradation in the photocatalytic layer unit.

FIG. 10 shows a kinetic curve of photocatalytic degradation of benzene by the photocatalytic layer unit 31. It can be seen from FIG. 10 that the TiO2 photocatalyst has high photocatalytic removal efficiency for benzene. The reduction in the concentration of benzene is relatively quick in the early stage of reaction, and gradually becomes gentle in the later stage of reaction. This may be because benzene adsorbed in advance on the activated carbon fiber mesh 313 is photocatalytically degraded by TiO2 at the beginning, and the adsorption capability of the activated carbon fiber mesh 313 is regenerated. The regenerated activated carbon fiber mesh 313 continuously adsorbs new benzene. At this time, adsorption and photocatalysis take place simultaneously. When the rate of adsorbing pollutants onto the activated carbon fiber mesh 313 and the rate of photocatalytically degrading pollutants on the surface of TiO2 are balanced, the degradation rate reaches a maximum value, and adsorption and photocatalysis are not performed cyclically. At this time, the degradation curve becomes relatively flat. With the increase of the reaction time, the benzene removal rate is increased obviously. When the reaction time is 120 min, the degradation rate reaches 88.9%. It can be seen that the photocatalyst has very high removal efficiency for volatile organic matters represented by benzene. It is indicated that, by using the activated carbon fiber mesh 313 as a carrier-loaded TiO2 catalyst, low-concentration organic pollutants in air in the room are quickly adsorbed due to the adsorption performance of the activated carbon fiber mesh. The pollutants adsorbed onto the surface of the activated carbon fiber mesh 313 are transferred to the surface of the TiO2 photocatalyst by surface transfer or in other ways and then photocatalytically degraded. Thus, the activated carbon fiber mesh 313 is regenerated in situ, that is, TiO2 on the TiO2 photocatalyst has the capability to regenerate the activated carbon fiber mesh 313 in situ.

Further, a WIFI unit is further arranged in the housing, and the WIFI unit is in bidirectional communication with the main control board 2. A user may log in a specific APP, and then connect to the robot body 1 through the WIFI unit, so as to control the operation of each module in real time. For example, if it is required to control the electric mosquito-repelling liquid evaporation unit 33 to be turned off, the main control board 2 will control a port corresponding to the electric mosquito-repelling liquid evaporation unit 33 to be powered off, so that the electric mosquito-repelling liquid evaporation unit 33 stops operating.

Further, a cylindrical sleeve 8 is helically mounted at the air inlet 11 in the housing, and internal threads are formed on an inner wall of the cylindrical sleeve 8. An external thread is formed on an outer sidewall of the front filter screen 7. The external thread on the front filter screen 7 is fitted with the internal threads on the inner wall of the cylindrical sleeve 8 to realize detachable connection. When in use for a certain period of time, the filtering capability of the front filter screen 7 is definitely reduced, so that the cylindrical sleeve 8 may be unscrewed to allow the front filter screen 7 to be detached from the cylindrical sleeve 8 for replacement.

The foregoing implementations are merely preferred implementations of the present utility model and not intended to limit the scope of the present utility model. Various variations and improvements made to the technical solutions of the present utility model by a person of ordinary skill in the art without departing from the design spirit of the present utility model shall fall into the protection scope defined by the claims of the present utility model.

What is claimed is:

1. An intelligent air purification robot with a mosquito-repelling function, comprising a robot body that has an obstacle detection function and can make a turn automatically, characterized in that the robot body comprises a housing with an air inlet and an air outlet, an insecticidal purification component arranged in the housing, a power supply unit arranged in the housing, and a main control board that is electrically connected to the power supply unit and arranged in the housing; the insecticidal purification component comprises a front filter screen, a fan unit, a black light lamp unit, a photocatalytic layer unit, an anion generator, an ozone generator and an electric mosquito-repelling liquid evaporation unit; the front filter screen is detachably mounted at the air inlet, and both the anion generator and the ozone generator are detachably mounted at the air outlet; several pairs of mounting seats that are symmetrical in an up-down direction are arranged in the robot body, and mounting holes corresponding to the mounting seats are formed in a sidewall of the robot body; the photocatalytic layer unit, the black light lamp unit, the electric mosquito-repelling liquid evaporation unit and the fan unit are successively arranged in parallel in a direction from the air inlet to the air outlet, and pass through the mounting holes to be detachably mounted on the respective mounting seats; the black light lamp unit, the fan unit and the electric mosquito-repelling liquid evaporation unit are all electrically connected to the main control board; the insecticidal purification component further comprises a hollow electric telescopic rod component; one end of the electric telescopic rod component is electrically connected to the main control board, and the other end thereof extends outside the housing to be connected to a UV lamp; and, the UV lamp passes through the inside of the electric telescopic rod component through a lead wire and is electrically connected to the main control board.

2. The intelligent air purification robot with a mosquito-repelling function according to claim 1, characterized in that a groove, which extends along the length of the mounting seat and has a longitudinal section shaped as an isosceles trapezoid, is formed on the surface of each mounting seat; the fan unit comprises an exhaust fan and fan horizontal mounting frames mounted at upper and lower ends of the exhaust fan; each fan horizontal mounting frame has a longitudinal section matched with that of the groove; and, the fan horizontal mounting frames at the upper and lower ends of the exhaust fan are inserted into the grooves on the mounting seats and slide along the grooves.

3. The intelligent air purification robot with a mosquito-repelling function according to claim 2, characterized in that a first fan vertical mounting frame is mounted on one side of the exhaust fan, a fan quick-fit male terminal is arranged on the first fan vertical mounting frame, and the exhaust fan is electrically connected to the fan quick-fit male terminal; a fan quick-fit female terminal corresponding to the fan quick-fit male terminal is arranged on the main control board; a second fan vertical mounting frame is mounted on the other side of the exhaust fan; the fan horizontal mounting frames at the upper end and the lower end of the exhaust fan pass through the mounting holes to be inserted into the grooves on the mounting seats; the fan quick-fit male terminal is electrically connected to the fan quick-fit female terminal; and, the second fan vertical mounting frame is hermetically arranged in the mounting holes.

4. The intelligent air purification robot with a mosquito-repelling function according to claim 3, characterized in that a fan push-pull handle is further arranged on a side of the second fan vertical mounting frame facing the outside of the housing.

5. The intelligent air purification robot with a mosquito-repelling function according to claim 2, characterized in that the black light lamp unit comprises a sealing cover plate, a mounting cover plate, and a plurality of black light lamps that extend along a lengthwise direction of the mounting seats and arranged from the top down; clamping slots equal in number to the black light lamps are formed on one side of the mounting cover plate, and the sealing cover plate is fixed on the other side of the mounting cover plate; one end of each of the plurality of black light lamps is inserted into the clamping slot, and a black light lamp quick-fit male terminal is arranged at the other end of the black light lamp; black light lamp quick-fit female terminals corresponding to the black light lamp quick-fit male terminals are arranged on the main control board; upper and lower ends of the mounting cover plate have longitudinal sections of an isosceles trapezoid structure; the upper and lower ends of the mounting cover plate are inserted into the grooves on the mounting seats; the black light lamp quick-fit male terminals of the black light lamps are electrically connected to the black light lamp quick-fit male terminals; and, the sealing cover plate is hermetically covered on the mounting holes.

6. The intelligent air purification robot with a mosquito-repelling function according to claim 5, characterized in that a black light lamp push-pull handle is further arranged on a side of the sealing cover plate facing the outside of the housing.

7. The intelligent air purification robot with a mosquito-repelling function according to claim 2, characterized in that the electric mosquito-repelling liquid evaporation unit comprises a support grid, an electric mosquito-repelling liquid evaporator, and mosquito-repelling horizontal mounting frames mounted at upper and lower ends of the support grid, and the mosquito-repelling horizontal mounting frames have longitudinal sections matched with that of the grooves; a first mosquito-repelling vertical mounting frame is mounted on one side of the support grid; a mosquito-repelling quick-fit male terminal is arranged on the first mosquito-repelling vertical mounting frame; a clamping hole for clamping the electric mosquito-repelling liquid evaporator is formed in the center of the support grid; the electric mosquito-repelling liquid evaporator is clamped in the clamping hole and electrically connected to the mosquito-repelling quick-fit male terminal through a lead wire; a mosquito-repelling quick-fit female terminal corresponding to the mosquito-repelling quick-fit male terminal is arranged on the main control board; a second mosquito-repelling vertical mounting frame is mounted on the other side of the support grid; the mosquito-repelling horizontal mounting frame is inserted into the grooves on the mounting seats and slide along the grooves; the mosquito-repelling quick-fit male terminal is electrically connected to the mosquito-repelling quick-fit female terminal; the second mosquito-repelling vertical mounting frame is hermetically arranged in the mounting holes; and, a mosquito-repelling push-pull handle is arranged on a side of the second mosquito-repelling vertical mounting frame facing the outside of the housing.

8. The intelligent air purification robot with a mosquito-repelling function according to claim 2, characterized in that the photocatalytic layer unit comprises an activated carbon fiber mesh coated with a $TiO_2$ photocatalyst; photocatalytic layer horizontal mounting frames are mounted at upper and lower ends of the activated carbon fiber mesh, and the photocatalytic layer horizontal mounting frames have longitudinal sections matched with that of the grooves; a first photocatalytic layer vertical mounting frame is mounted on one side of the activated carbon fiber mesh, and a second photocatalytic layer vertical mounting frame is mounted on the other side of the electric mosquito-repelling liquid evaporator; the photocatalytic layer horizontal mounting frames located at the upper and lower ends of the activated carbon fiber mesh are inserted into the grooves on the mounting seats and slide along the grooves; the second photocatalytic layer vertical mounting frame is hermetically arranged in the mounting holes; and, a photocatalytic layer push-pull handle is arranged on a side of the second photocatalytic layer vertical mounting frame facing the outside of the housing.

9. The intelligent air purification robot with a mosquito-repelling function according to claim 1, characterized in that a WIFI unit is further arranged in the housing, and the WIFI unit is in bidirectional communication with the main control board.

10. The intelligent air purification robot with a mosquito-repelling function according to claim 1, characterized in that a cylindrical sleeve is helically mounted at the air inlet on the housing; internal threads are formed on an inner wall of the cylindrical sleeve; an external thread is formed on an outer sidewall of the front filter screen; and, the external thread on the front filter screen is fitted with the internal threads on the inner wall of the cylindrical sleeve to realize detachable connection.

* * * * *